United States Patent [19]

Hung et al.

[11] Patent Number: 5,350,497
[45] Date of Patent: Sep. 27, 1994

[54] PRODUCTION OF PERFLUORO (ALKYL VINYL ETHERS)

[75] Inventors: Ming-Hong Hung, Wilmington, Del.; Shlomo Rozen, Tel Aviv, Israel

[73] Assignee: E. I. Du Pont de Nemours and Company, Wilmington, Del.

[21] Appl. No.: 65,975

[22] Filed: May 21, 1993

[51] Int. Cl.$^5$ ............................................. C07C 41/00
[52] U.S. Cl. .......................... 204/157.92; 204/157.94; 204/157.98; 568/685
[58] Field of Search ............... 204/157.92, 157.94, 204/157.98; 568/685

[56] References Cited

U.S. PATENT DOCUMENTS 4,533,741  8/1985  Squire ................................. 549/455
4,908,461  3/1990  Hung .................................. 549/455

FOREIGN PATENT DOCUMENTS 4-247049  9/1992  Japan .

*Primary Examiner*—John Niebling
*Assistant Examiner*—Cybille Delacroix-Muirheid

[57] ABSTRACT

Disclosed herein is a process for making perfluoro(alkyl vinyl ethers) by fluorination with elemental fluorine of selected novel partially fluorinated (di)chloroethyl ethers, followed by dehalogenation to the corresponding perfluoro(alkyl vinyl ether). The perfluoro(alkyl vinyl ethers) are useful as monomers for molding resins and elastomers.

16 Claims, No Drawings

PRODUCTION OF PERFLUORO (ALKYL VINYL ETHERS)

FIELD OF THE INVENTION

This invention concerns a process for making perfluoro(alkyl vinyl ethers) in which a specified partially fluorinated compound containing a chlorine substituted ethoxy group is fluorinated with elemental fluorine, and the product of that reaction is dehalogenated to form the desired product. Also disclosed are novel intermediates in this synthesis.

TECHNICAL BACKGROUND

Perfluoro(alkyl vinyl ethers) (herein sometimes abbreviated as PAVE) are present as monomeric units in a number of polymers which are commercially available, particularly perfluorinated thermoplastics useful as molding resins, and elastomers useful for heat and solvent resistant seals, and other uses. These ethers can be made by several methods, such as the pyrolysis of an appropriate acyl fluoride. However these methods often have disadvantages, such as only moderate yields, unwanted isomeric byproducts, and/or byproducts that are environmentally deleterious. Therefore, improved synthesis methods for these compounds are of interest.

SUMMARY OF THE INVENTION

This invention concerns a process for the production of perfluoro(alkyl vinyl ethers), comprising, fluorinating with elemental fluorine a first compound of the formula

to form a second compound of the formula $R^2CF_2OCFX^2CF_2X^2$ and dehalogenating said second compound to form a perfluoro(alkyl vinyl ether) of the formula $R^2CF_2OCF=CF_2$ wherein:
- $R^1$ is hydrogen, a fluorinated alkyl group, or a fluorinated alkyl group containing one or more ether oxygen atoms between alkylene segments;
- each $X^1$ and $X^3$ is independently hydrogen or fluorine;
- in said first compund each $X^2$ is independently chlorine, bromine, iodine or fluorine, provided that at least one of $X^2$ is chlorine;
- in said second compound each $X^2$ is independently chlorine or fluorine, provided that at least one of $X^2$ is chlorine; and
- $R^2$ is fluorine, perfluoroalkyl, or perfluoroalkyl containing one or more ether oxygen atoms between alkylene segments.

This invention also concerns a compound of the formula

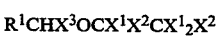

wherein:
- $R^1$ is hydrogen, a fluorinated alkyl group, or a fluorinated alkyl group containing one or more ether oxygen atoms between alkylene segments;
- each $X^1$ and $X^3$ is independently hydrogen or fluorine; and
- each $X^2$ is independently chlorine, bromine, iodine or fluorine provided that at least one of $X^2$ is chlorine.

DETAILS OF THE INVENTION

The starting material for the process of preparing PAVEs described herein is $R^1CHX^3OCX^1X^2CX^1{}_2X^2$, wherein $R^1$, $X^1$, $X^2$ and $X^3$ are as described above. In preferred starting materials $R^1$ is perfluoroalkyl, $H(CF_2)_n$— where n is 1 to 20, hydrogen, or perfluoroalkyl containing one or more ether oxygen atoms between alkylene segments. In more preferred embodiments, $R^1$ is $F(CF_2)_n$— where n is 1 to 20, hydrogen, or $C_3F_7O[CF(CF_3)CF_2O]_yCF(CF_3)$—, wherein y is 0 or an integer of 1 to 8. In other preferred embodiments, each $X^1$ is fluorine, and/or each $X^2$ is chlorine, and/or $X^3$ is hydrogen. In all cases, it is also preferred if $R^1$ contains 1 to 30 carbon atoms (except where otherwise specified).

By a (per)fluorinated alkyl group containing one or more ether oxygen atoms between alkylene segments is meant an alkyl group which is "interrupted" with one or more ether oxygen atoms between carbon atoms of the (per)fluorinated alkyl group. In effect, the ether oxygen atoms "split" the alkyl group up into a radical containing one or more alkylene groups. A typical ether containing (per)fluoroalkyl group is $C_3F_7O[CF(CF_3)C$-$F_2O]_yCF(CF_3)$—, wherein y is 0 or an integer of 1 to 8.

When using all of the preferred embodiments listed above for each variable in the compound $R^1CHX^3OCX^1X^2CX^1{}_2X^2$, the synthesis of the PAVE can be done using the following reaction sequence:

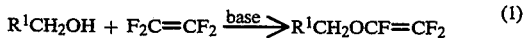

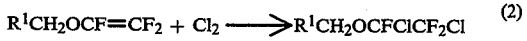

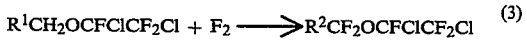

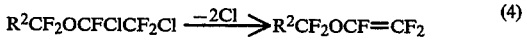

Reactions 3 and 4 are the two steps of Claim 1, while reactions (1) and (2) illustrate how the starting material can be obtained for reaction (3). Many of the starting alcohols for reaction (1) are commercially available. Reaction 2 is simply a chlorination of the double bond of the trifluorovinyl ether formed in reaction 1. Variations in this synthesis to make the other compounds included as starting materials for the fluorination reaction will be evident to the art skilled. Many of these reactions are also illustrated in the Examples.

Reaction (2), the halogenation reaction, may conveniently be carried out at $-10°$ to $+50°$ C., preferably 0° to 30° C. The temperature of the halogenation should be kept low enough so that replacement of hydrogen by halogen is avoided. To obtain the compound where one of $X^2$ is not chlorine, ClF, BrCl or ICl may be used. It is preferred if chlorine is used in the halogenation. Use of a solvent is optional, such solvent being inert to chlorine, such as 1,1,2-trichloro-1,2,2-trifluoroethane and carbon tetrachloride. The reaction is preferably done under an inert atmosphere such as nitrogen, and is agitated to mix the reactants. The product, if sufficiently volatile, may be purified by distillation. Other variations known to the artisan may also be used.

Reaction (3), the fluorination, should be carried out so that all hydrogen atoms are replaced by fluorine, but under conditions mild enough so that the carbon skeleton of the starting material is not disturbed and the chlorine atoms are not replaced by fluorine. Usually, if one of $X^2$ is bromine or iodine, these halogen atoms will be replaced by fluorine. Such methods are, in general, known to the artisan. This can be done at a temperature of about $-30°$ C. to about $+50°$ C., preferably $-20°$ to $+10°$ C., more preferably $-10°$ to $0°$ C. A solvent substantially inert to fluorine should be used, such as Krytox®-GPL (a fluorinated liquid available from E. I. du Pont de Nemours and Company, Wilmington, Del., USA) or perfluoro(2-butyltetrahydrofuran). In order to moderate the reaction of fluorine with the substrate, a mixture of fluorine and an inert gas such as nitrogen should preferably be used, for instance 25 volume percent fluorine and 75 volume percent nitrogen. Agitation sufficient to efficiently mix the reactants should be used. In a preferred embodiment the reaction ingredients are irradiated with ultraviolet light. The reaction should be run in such an apparatus that the ultraviolet radiation reaches the reaction mixture. It is believed that exposure to ultraviolet radiation makes the reaction proceed more rapidly. Inorganic fluorides, such as NaF may be added to absorb the byproduct HF. If sufficiently volatile, the product may be purified by distillation.

The dehalogenation reaction, reaction (4), is carried out using a metal or a metal containing reducing agent. Such reactions are known to the artisan. References which describe such reactions include U.S. Pat. Nos. 4,533,741, 4,908,461 and M. Hudlicky, Chemistry of Organic Fluorine Compounds, Ellis Norwood, New York, N.Y., p. 483–484 (1992). Useful metals include zinc, magnesium and copper, and useful metal containing reducing agents include $TiCl_4/LiAlH_4$. Reaction conditions will generally be milder when 2 chlorine atoms are removed to form the PAVE than when one chlorine atom and one fluorine atom are removed to form the PAVE. Reaction conditions will also vary depending on which metal or metallic reducing agent is used. For instance, when removing 2 chlorine atoms, using zinc a useful temperature range is about $40°$ C. to about $160°$ C., preferably $80°$ to $140°$ C., while when using $TiCl_4/LiAl_4$ a useful temperature range is about $0°$ C. to about $+30°$ C., preferably $5°$ to $25°$ C. For all of these dehalogenation reactions an aprotic polar solvent is desirable, whose choice depends upon the reagents to be used. Useful solvents including N,N-dimethylformamide, acetic anhydride, p-dioxane, and tetrahydrofuran. Agitation should be employed to mix the reactants efficiently, and it is preferred if the reaction is done under an inert atmosphere such as nitrogen. If sufficiently volatile, the product PAVE may be purified by distillation.

Also disclosed herein is a compound of the formula $R^1CHX^3OCX^1{_2}CX^1{_2}X^2$, wherein $R^1$, $X^1$, $X^2$ and $X^3$ are as defined above. Preferred groups and/or structures for $R^1$, $X^1$, $X^2$ and $X^3$ are as described above for the process disclosed herein. This novel compound is useful as an intermediate in the preparation of PAVEs.

EXPERIMENT 1

Preparation of 1,1-Dihydropentafluoropropyl Trifluorovinyl Ether

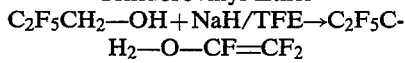

NaH (60% oil suspension, 48 g, 1.2 mol) was suspended in anhydrous 1,4-dioxane (600 mL) in a glass r.b. flask. Pentafluoropropanol was added slowly while the pot was kept at $15°–20°$ C. with external cooling. After addition, the mixture was stirred at ambient temperature for 1–2 hr. This pentafluoropropanol salt solution was then transferred into a 1-liter autoclave, sealed, and heated for 20 hr at $100°$ C. The autoclave was cooled, evacuated, and was pressured with tetrafluoroethylene (TFE) to 2.1 MPa. The reaction was allowed to proceed for 40 hr at $30°–35°$ C. while maintaining the TFE pressure at 2.1 MPa.

The product mixture was dumped into ice water and the organic layer was separated, washed with water twice, then distilled to afford the desired product (128 g, 62% yield) as a clear, colorless liquid, bp. $87°–88°$ C. $^1H$ NMR (300 MHz, $CDCl_3$): $\delta4.36$ (t, J=12.4 Hz); $^{19}F$ NMR (188.24 MHz, $CFCl_3$): $-84.2$ (3 F), $-125.1$ (t, J=12.4 Hz, 2 F), $-120.8$, $-121.1$, $-121.3$, $-121.6$ (4 d, 1 F), $-126.6$, $-127.1$, $-127.2$, $-127.7$ (4 s, 1 F), $-137.8$, $-138.1$, $-138.3$, $-138.7$ (4 s, 1 F). A Small amount of 1,1-dihydropentafluoropropyl 2-hydrotetrafluoroethyl ether ($C_2F_5CH_2OCF_2CF_2H$) was also obtained from the reaction.

EXPERIMENT 2

Preparation of 1,1-Dihydropentafluoropropyl 2-Chlorodifluorovinyl Ether

The sodium salt solution of pentafluoropropanol was prepared from NaH (60% oil suspension, 42.8 g, 1.07 mol) and $C_2F_5CH_2OH$ (120 g, 0.8 mol) in 1,4-dioxane (500 mL) according to that described in Experiment 1. This salt solution was transferred into the 1-liter autoclave and was heated at $100°$ C. for 16 h. After being cooled and evacuated, chlorotrifluoroethylene (CTFE) was charged into the reactor. The reaction was allowed to proceed for 30 hr at $40°$ C. while maintaining CTFE pressure at 482 kPa during the process. After workup and distillation, the desired product was obtained as a clear, colorless liquid, bp. $91°–93°$ C., yield 90 g (45.6%). This product is an E/Z isomer mixture (molar ratio: 1.38:1.00). $^1H$ NMR (300 MHz, $CDCl_3$): $\delta4.38$ (m); $^{19}F$ NMR (188.24 MHz, $CFCl_3$): $-84.0$ (E), $-84.1$ (Z) [2 s, 3 F total], $-124.8$ (m, 2 F total), $[-107.0$ (d, J=41 Hz) (E), $-129.7$ (d, J=41 Hz) (E), $-122.0$ (d, J=120 Hz) (Z), $-135.3$ (d, J=120 Hz) (Z)](2 F total).

Anal. Calcd. for $C_5H_2F_7ClO$: C: 24.36, H: 0.82, Cl: 14.38; Found: C: 23.92, H: 0.78, Cl: 14.15.

EXAMPLE 3

Preparation of 1,1-Dihydropentafluoropropyl 2-Hydrodifluorovinyl Ether

This compound was prepared in the way similar to that described in Experiment 1 from pentafluoropropanol (120 g, 0.8 mol), NaH (60% oil suspension, 42.8 g, 1.07 mol) and trifluoroethylene (140 g, 1.71 mol)

in anhydrous 1,4-dioxane (500 mL). The desired product was isolated as a clear, colorless liquid, bp. 68°–71° C., yield 70 g (41.3%). This product is an E/Z isomer mixture (molar ratio: 2:1). $^1$H NMR (300 MHz, CDCl$_3$): δ[6.70 (dd, J=72 Hz, 4.2 Hz) (E), 6.50 (dd, J=72 Hz, 14.8 Hz) (Z)] (1H total), [4.46 (t, J=12.3 Hz) (E), 4.32 (t, J=12.3 Hz) (Z)] (2H total); $^{19}$F NMR (188.24 MHz, CFCl$_3$): −84.1 (s, br, 3F), [−125.0 (t, J=12.3 Hz) (E), −124.6 (t, J=12.3 Hz) (Z) ] (2 F total), [−131.9 (d, J=121.6 Hz) (E), −106.7 (t, J=14.8 Hz) (Z)] (1 F total), [−196.3 (dd, J=121.7 Hz, 72.8 Hz), −189.5 (dd, J=15.9 Hz, 72.1 Hz)](1 F total). Anal. Calcd. for C$_5$H$_3$F$_7$O: C: 28.30, H: 1.43; Found: C: 27.70, H: 1.19. MS: m/e: 212.

EXPERIMENT 4

Preparation of 1,1-Dihydrotrifluoroethyl Trifluorovinyl Ether $$CF_3CH_2\text{—}OH + NaH/TFE \rightarrow CF_3CH_2\text{—}O\text{—}CF\text{=}CF_2$$

This compound was prepared according to the procedures of Experiment 1 from NaH (60% oil suspension, 48 g, 1.2 mol) and trifluoroethanol (100 g, 1.0 mol) in anhydrous 1,4-dioxane (500 mL) under 2.1 MPa TFE pressure. After workup, the title compound was obtained as a clear, colorless liquid, bp. 43°–44° C. yield 44 g. $^1$H NMR (300 MHz, CDCl$_3$): δ4.26 (m); $^{19}$F NMR (188.24 MHz, CFCl$_3$): −75.4 (t, J=7.9 Hz, 3 F), −121.0, −121.3, −121.5, −121.8 (4 s, 1 F), −127.0, −127.5, −127.6, −128.0 (4 d, J=1.7 Hz, 1 F), −137.6, −137.9, −138.2, −138.5 (4 s, 1 F).

EXPERIMENT 5

Preparation of 1,1-Dihydrotrifluoroethyl 2-Chlorodifluorovinyl Ether $$CF_3CH_2\text{—}OH + NaH/CF_2\text{=}CFCl \rightarrow CF_3CH_2\text{—}O\text{—}CF\text{=}CFCl$$

This compound was prepared according to the procedures of Experiment 2 from NaH (60% oil suspension, 42.8 g, 1.07 mol) and trifluoroethanol (80 g, 0.8 mol) and chlorotrifluoroethylene (160 g) in anhydrous 1,4-dioxane (500 mL). After workup, the product was purified by distillation. The title compound was isolated as a clear, colorless liquid, bp. 75° C., yield 62 g (40%). This product was an E/Z isomer mixture (molar ratio: 1.33:1.00). $^1$H NMR (300 MHz, CDCl$_3$): δ4.32 (m); $^{19}$F NMR (188.24 MHz, CFCl$_3$): [−75.0 (t, J=7.8 Hz) (E), −75.3 (t, J=7.8 Hz) (Z)] (3 F total), [−106.9 (d, J=40.8 Hz) (E), −129.9 (d, J=40.8 Hz) (E) , −121.8 (d, J=119.4 Hz) (Z), −135.5 (d, J=119.4 Hz) (Z)] (2 F total). Anal. Calcd. for C$_4$H$_2$F$_5$ClO: C: 24.45, H: 1.03, Cl: 18.04 , F: 48.34; Found: C: 24.36, H: 1.03, Cl: 17.62, F: 48.18. Mass for [M]: Calc: 195.9640; Found: 195.9677.

EXPERIMENT 6

Preparation of 1,1-Dihydrotrifluoroethyl 2-Hydrodifluorovinyl Ether $$CF_3CH_2\text{—}OH + NaH/CF_2\text{=}CFH \rightarrow CF_3CH_2\text{—}O\text{—}CF\text{=}CFH$$

This compound was prepared in the way similar to that described in Experiment 3 from NaH (60% oil suspension, 42.8 g, 1.07 mol) trifluoroethanol (80 g, 0.8 mol) and trifluoroethylene (160 g) in anhydrous 1,4-dioxane (500 mL). The reaction proceeded for 30 hr at 40° C. After workup, a clear, colorless liquid was obtained, bp. 54°–56° C., yield 50 g. The structure of this compound was confirmed by its NMR spectra. This product was an E/Z isomer mixture (molar ratio: 2.4:1).

$^1$H NMR (300 MHz, CDCl$_3$): δ[6.70 (dd, J=72 Hz, 4.0 Hz) (E), 6.50 (dd, J=72 Hz, 14.8 Hz) (Z)] (1H total), [4.34 (m) (E), 4.23 (m) (Z)] (2H total); $^{19}$F NMR (188.24 MHz, CFCl$_3$): [−75.4 (t, J=7.9 Hz) (E) , −74.9 (t, J=8.0 Hz) (Z)] (3 F total), [−131.7 (d, J=121.6 Hz) (E), −106.4 (t, J=14.8 Hz) (Z)] (1 F total), [−196.4 (dd, J=121.7 Hz, 72.8 Hz), −189.7 (dd, J=15.9 Hz, 72 Hz)] (1 F total). Anal. Calcd. for C$_4$H$_3$F$_5$O: C: 29.63, H: 1.87, F: 58.63; Found: C: 28.99, H: 1.75, F: 58.69. Mass for [M]: Calc: 162.0042; Found: 162.0115.

EXPERIMENT 7

Preparation of 1,1-Dihydro-2,5-Bis(trifluoromethyl)-3,6-Dioxa-2,4,4,5,7,7,8,8,9,9,9-Undecafluorononyl Vinyl Ether $$C_3F_7O\text{—}CF(CF_3)CF_2O\text{—}CF(CF_3)\text{—}CH_2OH \rightarrow C_3F_7O\text{—}CF(CF_3)CF_2O\text{—}CF(CF_3)\text{—}CH_2OCH\text{=}CH_2$$

This compound was prepared from hexafluoropropylene oxide trimer according to U.S. Pat. No. 4,568,773. The alcohol substrate (96.4 g, 0.2 mol), vinyl acetate (86 g, 1.0 mol) and mercuric acetate (0.5 g) were mixed at 0° C. with vigorous stirring. Concentrated sulfuric acid (25–50 μL) was added and the reaction was allowed to proceed for 6–8 hr at 0°–10° C. Potassium carbonate (3 g) was added to terminate the reaction and the product mixture was fractionally distilled, and the product boiling between 30° to 100° C. at 2.7 kPa was collected. Potassium hydroxide (12 g) was added to destroy the residual vinyl acetate present in the distillate. A second distillation gave the desired vinyl ether 30 g as a clear, colorless liquid, bp. 148°–152° C. $^1$H NMR (300 MHz, CDCl$_3$): δ6.46 (m, 1H), 4.28 (dm, J=15 Hz, 1H), 4.20 (m, 3H); $^{19}$F NMR (188.24 MHz, CFCl$_3$): −80.7 (m, br, 3 F), −82.1 (m, 3 F), −83.4 (m, 3 F), −79.3 to −85.3 (m, 4 F), −130.3 (s, 2 F), −134.2 (m, 1 F), −145.8 (m, 1 F); MS: m/e: 508.

EXPERIMENT 8

Preparation of 1,1,5-Trihydrooctafluoropentyl Trifluorovinyl Ether $$H(CF_2)_4\text{—}CH_2\text{—}OH + NaH/TFE \rightarrow H(CF_2)_4CH_2\text{—}O\text{—}CF\text{=}CF_2$$

The alcohol sodium salt was prepared from NaH (60% oil suspension, 32 g, 0.8 mol) and 2,2,3,3,4,4,5,5-octafluoropentan-1-ol (139.2 g, 0.6 mol) in anhydrous ether solvent (600 mL) in a 1-liter reactor. The reactor was cooled, evacuated, and TFE was charged into the reactor. The reaction was allowed to proceed 24 hr at 50° C. while maintaining TFE pressure at 2.4 MPa during the process. After workup and distillation, the title compound was obtained as a clear liquid, bp. 56°–57° C. at 8.0 kPa, yield 115 g (61.4%). $^1$H NMR (300 MHz, CDCl$_3$): δ6.05 (tt, J=54.6 Hz, 5.4 Hz, 1H), 4.39 (t, J=12.6 Hz, 2H); $^{19}$F NMR (188.24 MHz, CFCl$_3$): −121.4 (br, 2 F), −125.7 (s, 2 F), −130.4 (s, 2 F), −137.7 (d, J=55 Hz, 2 F), −121.2 (m, 1 F), −127.0 (m, 1 F), −138.3 (m, 1 F).

EXPERIMENT 9

Preparation of 1,1,3-Trihydrotetrafluoropropyl Trifluorovinyl Ether $$H(CF_2)_2\text{—}CH_2\text{—}OH + NaH/TFE \rightarrow H(CF_2)_2CH_2\text{—}O\text{—}CF\text{=}CF_2$$

The compound was prepared from NaH (60% oil suspension, 20 g, 0.5 mol) and 2,2,3,3-tetrafluoropentan-1-ol (52.8 g, 0.4 mol) in anhydrous ether solvent (200 mL) under 2.4 MPa of TFE as described in Experiment 8. $^1$H NMR (300 MHz, CDCl$_3$): δ5.94 (tt, J=53.5 Hz, 8.4 Hz, 1H), 4.33 (dt, J=1.2 Hz, J=12.0 Hz, 2H); $^{19}$F NMR (188.24 MHz, CFCl$_3$): −121.1, −121.3, −121.5, −121.7 (4 s, 1 F), −125.6 (t, J=12.0 Hz, 2 F), −127.3, −127.6, −127.7, −128.0 (4 s, 1 F), −137.4, −137.7, −137.8, −138.0 (4 s, 1 F), −139.0 (d, J=53.5 Hz, 2 F).

EXAMPLE 1

Preparation of 1,1-Dihydropentafluoropropyl 1,2-Dichlorotrifluoroethyl Ether
$C_2F_5CH_2—O—CF=CF_2+Cl_2\rightarrow C_2F_5CH_2—O—CF-Cl—CF_2Cl$ The neat vinyl ether (75 g, 0.326 mol) from Experiment 1 was chlorinated with chlorine gas at 10°–15° C. The reaction was monitored by gas chromatography and was stopped when the conversion of the starting material was complete. The product was purified by distillation and afforded the title compound as a clear, colorless liquid bp. 95°–96° C., yield 86 g (88%) $^1$H NMR (300 MHz, CDCl$_3$): δ4.44 (m); $^{19}$F NMR (188.24 MHz, CFCl$_3$): −69.6 (d, J=6.2 Hz, 2 F), −74.8 (s, br, 1 F), −84.2 (s, 3 F), −123.9 (t, J=11.8 Hz, 2 F). Anal. Calcd. for $C_5H_2Cl_2F_8O$: C: 19.95, H: 0.67, Cl: 23.56, F: 50.50; Found: C: 19.95, H: 0.65, Cl: 22.97, F: 50.60. Mass m/e: 215 [M-CF$_2$Cl], 281 [M-F], 265 [M-Cl].

EXAMPLE 2

Preparation of 1,1-Dihydrotrifluoroethyl 1,2-Dichlorotrifluoroethyl Ether
$CF_3CH_2—O—CF=CF_2+Cl_2\rightarrow CF_3CH_2—O—CF-Cl—CF_2Cl$ The neat vinyl ether (25 g, 0.139 mol) from Experiment 4 was chlorinated with chlorine gas at 10°–15° C. The reaction was monitored by gas chromatography and was stopped when the conversion of the starting material was complete. The product was purified by distillation and afforded the title compound as a clear, colorless liquid, bp. 82°–84° C., yield 28 g (80%). $^1$H NMR (300 MHz, CDCl$_3$): δ4.38 (m) ; $^{19}$F NMR (188.24 MHz, CFCl$_3$): −69.6 (d, J=5.3 Hz, 2 F), −74.1 (s, br, 1 F), −74.4 (m, 3 F). Anal. Calcd. for $C_4H_2Cl_2F_6O$: C: 19.14, H: 0.80, Cl: 28.25; Found: C: 19.27, H: 0.80, Cl: 27.77. Mass m/e: 215 [M-Cl].

EXAMPLE 3

Preparation of 1,1,5-Trihydrooctafluoropentyl 1,2-Dichlorotrifluoroethyl Ether
$H(CF_2)_4CH_2—O—CF=CF_2+Cl_2\rightarrow H(CF_2)_4CH_2—O—CFCl—CF_2Cl$ The neat vinyl ether (50 g, 0.16 mol) from Experiment 8 was chlorinated with chlorine gas at 10°–15° C. The reaction was monitored by gas chromatography and was stopped when the conversion of the starting material was complete. The product was purified by distillation and afforded the title compound as a clear, colorless liquid, bp. 108°–110° C./6.7 kPa, yield 34 g (56%). $^1$H NMR (300 MHz, CDCl$_3$): δ6.06 (tt, J=52 Hz, 4.8 Hz, 1H), 4.48 (m, 2H); $^{19}$F NMR (188.24 MHz, CFCl$_3$): −69.6 (d, J=5.8 Hz, 2 F), −74.6 (s, br, 1 F), −120.1 (t, J=11.6 Hz, 2 F), −125.5 (s, 2 F), −130.3 (d, J=3.0 Hz, 2 F), −137.6 (dt, J=52 Hz, 2.7 Hz, 2 F). Anal. Calcd. for $C_7H_3Cl_2F_{11}O$: C: 21.95, H: 0.79, Cl: 18.51; Found: C: 21.91, H: 0.59, Cl: 18.03. Mass m/e: 347 [M-Cl].

EXAMPLE 4

Preparation of 1,1-Dihydrotrifluoroethyl 1,2-Dichloro-2-Hydrodifluoroethyl Ether
$CF_3CH_2—O—CF=CFH+Cl_2\rightarrow CF_3CH_2—O—CFCl—CFHCl$ The neat vinyl ether (50 g, 0.16 mol) from Experiment 6 was chlorinated with chlorine gas at 10°–15° C. as described in Examples 2 and 3. The product was purified by distillation and gave the title compound as a clear, colorless liquid, bp. 71°–73° C./2.9 kPa, yield 60 g (83.4%). This product was a mixture of two diastereomers (ratio 1.53:1.00). $^1$H NMR (300 MHz, CDCl$_3$): δ6.20 (dm, J=48 Hz, 1H), 4.37 (m, 2H); $^{19}$F NMR (188.24 MHz, CFCl$_3$): −74.4 (m, 4 F, CF$_3$+OCFCl), [−146.2, −147.3 (2 dd, J=17.3 Hz, 48.3 Hz; J=15.3 Hz, J=48.4 Hz)] (1 F total). Anal. Calcd. for $C_4H_3Cl_2F_5O$: C: 20.62, H: 1.30, Cl: 30.44, F: 40.78; Found: C: 20.76, H: 1.19, Cl: 30.26, F: 41.02. Mass m/e: 232 [M], 213 [M-F], 197 [M-Cl].

EXAMPLE 5

Preparation of 1,1-Dihydro-2,5-Bis (trifluoromethyl)-3,6-Dioxa-2,4,4,5,7,7,8,8,9,9,9-Undecafluorononyl 1,2-Dichloroethyl Ether
$C_3F_7O—CF(CF_3)CF_2O—CF(CF_3)—CH_2OH=CH_2+Cl_2\rightarrow C_3F_7O—CF(CF_3)CF_2O—CF(CF_3)—CH_2OCHCl—CH_2Cl$ The neat vinyl ether (16 g, 0.0315 mol) from Experiment 7 was chlorinated with chlorine gas at 10°–15° C. as described in Example 1. After workup and distillation, the title compound was isolated as a colorless liquid, bp. 91°–93° C./1.3 kPa, yield 16 g (88%). $^1$H NMR (300 MHz, CDCl$_3$): δ5.58 (m, 1H), 4.43 (t, J=11.4 Hz, 1H), 4.08 (m, 1H), 3.82 (m, 2H); $^{19}$F NMR (188.24 MHz, CFCl$_3$): −80.6 (s, br, 3 F), −82.0 (t, J=8.0 Hz, 3 F), −83.2 (2 s, 3 F), −79.2 to −85.2 (m, 4 F), −130.2 (d, J=0.5 Hz, 2 F), −134.3 (2 m, 1 F), −145.6 (m, 1 F) . Anal. Calcd. for $C_{11}H_5Cl_2F_{17}O_3$: C: 22.82, H: 0.87, Cl: 12.25, F: 55.78; Found: C: 22.84, H: 0.74, Cl: 12.15, F: 55.87. MS: m/e: 577 [M-H].

For Examples 6-8, $^1$H NMR spectra were recorded with a GEQE plus instrument at 300 MHz with CDCl$_3$ as solvent and Me$_4$Si as internal standard. The $^{19}$F NMR spectra were measured with an NIC 1180E instrument at 188.24 MHz and GEQE plus at 283.1 MHz and are reported in parts per million upfield from CFCl$_3$, which also served as internal standard. Mass spectra were measured with a VG micromass 7070H instrument. GC was done using a Hewlett Packard 5890 with a 25 m×0.2 mm HP1 crosslinked methyl silicon capillary column, operating at 60°–250° C.

General Procedure For Working With Fluorine

Fluorine is of course a strong oxidizer and a very corrosive material. An appropriate vacuum line made from copper or monel in a well ventilated area should be constructed for working with this element. The reactions themselves were carried out in Teflon vessels.

General Procedure Substituting Hydrogen with Fluorine (Examples 6-8)

Mixtures of 25%–30% (volume) F$_2$ diluted with nitrogen were used in this work. The gas mixtures were prepared in a secondary container before the reaction was started. The appropriate substrate was dissolved either in perfluoro2-butyl-THF (FC-75 from 3M Company) or in Krytox ®-GPL 100 (a fluorinated oil from DuPont Company) which also contained about 5 g of pulverized NaF to absorb the released HF. The reaction mixture was cooled to −10° C., stirred with the aid of a vibromixer and irradiated with a 450 W medium pressure mercury lamp. The reactions were monitored by GC/MS and were brought to completion. It was evident from the mass spectrum that the first hydrogen of the CH$_2$O group is quickly replaced, but the second one required a longer time. Usually a large excess of fluorine was used for the second hydrogen to be replaced but this fluorine could, in theory be used for a second reactor hooked in a series. Actually, the unreacted fluorine was trapped by passing it through soda lime trap. Because of reactor limitations it was evident that a considerable portion of both the substrate and the product are carried away by the continuous stream of nitrogen. This affected, somewhat artificially, the reaction yields. The yields reported are of isolated products. After the reaction was finished, the mixture was poured into water, washed with bicarbonate till neutral, the organic layer separated and dried over MgSO$_4$. The products were then distilled either under atmospheric or reduced pressure.

EXAMPLE 6

Preparation of perfluoropropyl 1,2-Dichlorotrifluoroethyl Ether

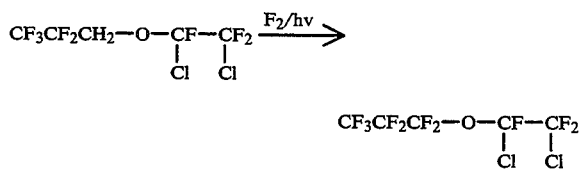

A cold solution (−10° C.) of the dichloro derivative from Example 1 (10 g) in Krytox ® was prepared. NaF (5 g) was added and the reaction was performed as described above. The crude product contained only solvent and a single product. It was distilled at 78°–80° C. and proved to be the desired product; yield 5.0 g (45%). No proton was detectable in the $^1$H NMR. $^{19}$F NMR: −71.5 (s, br, 2 F, CF$_2$Cl), −77.5 (narrow m, 1 F, CFCl), −82 (t, J=7 Hz, 3 F), −85.5 (m, 2 F, CF$_2$O), −130.7 (narrow m, 2 F, CF$_3$ CF$_2$ CF$_2$O); MS m/e 300. 9476 [(M-Cl)], (Calcd.: 300.9477); 168.9773 (CF$_3$CF$_2$CF$_2$)+(Calcd.: 168.9888); 150.9251, (CFClCF$_2$Cl)+(Calcd.: 150.9329). Anal. Calcd. for C$_5$F$_{10}$Cl$_2$O: C: 17.82, F: 56.38; Found: C: 17.57, F: 56.38.

EXAMPLE 7

Preparation of Perfluoropentyl 1,2-Dichlorotrifluoroethyl Ether

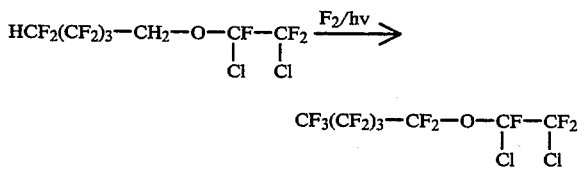

A cold solution (−10° C.) of the dichloro derivative from Example 3 (9.3 g) in Krytox ® was prepared. Sodium fluoride (5 g) was added and the reaction was performed as described above. The crude product contained only solvent and a single product. It was distilled at 92°–98° C. at 11 kPa and proved to be the desired product, yield 7.25 g (70%). No proton was detectable in the $^1$H NMR. $^{19}$F NMR: −71.27 (narrow m, 2 F, CF$_2$Cl), −77.17 (narrow m, 1 F, CFCl), −81.3 (narrow m, 3 F), −84.75 (m, 2 F, CF$_2$O), −123.55 and −126.17 (two narrow m, each 2 F (CF$_3$CF$_2$CF$_2$ CF$_2$ CF$_2$O), −126.79 (narrow m, 2 F, CF$_3$ CF$_2$ CF$_2$O); MS m/e 400.9407 [(M-Cl)], (Calcd.: 400.9414); 350.9456 [(M-CF$_2$Cl)+], (Calcd.: 350.9446); 150.8693 (CFClCF$_2$Cl)+, (Calcd.: 150.9329); 84.9684 (CF$_2$Cl)+, (Calcd.: 84.9657); Anal. Calcd. for C$_7$F$_{14}$Cl$_2$O: C: 19.24, F: 60.87; Found: C: 19.03, F: 61.35.

EXAMPLE 8

Preparation of Perfluoro-2,5-Bis(trifluoromethyl)-3,6-Dioxanonyl 1,2-Dichlorotrifluoroethyl Ether

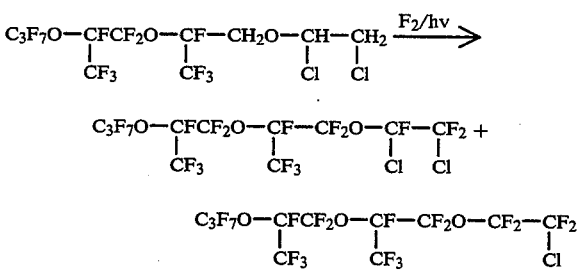

A cold solution (−10° C.) of the dichloro derivative from Example 5 (12 g) in FC-75 was prepared. Sodium fluoride (5 g) was added and the reaction was performed as described above. The crude product contained only solvent and two products in a ratio of 4:1. The solvent was first distilled followed by the products at 80°–100° C. at 16 kPa. The fractions which contained the desired material were distilled again on a spinning band column. The first fractions (99°–105° C./16 kPa) proved to be a mixture of the two products but the later ones (118° C./15 kPa) proved to be the pure major derivative. This major product, the dichloro compound, was obtained in 58% yield. No proton was detectable in the $^1$H NMR. $^{19}$F NMR: −71.47 (narrow m, 2 F, CF$_2$Cl), −77.3 (narrow m, 1F, CFCl), −79.9 to −85.7 (multiplets for 3CF$_3$ and 3CF$_2$O groups, 15 F), −130.3 (s, br, CF$_3$ CF$_2$ CF$_2$O, 2 F), −145.4 to −146.1 (m, two CF CF$_3$, 2 F); MS m/e 335 [(C$_3$F$_7$OCF(CF$_3$)CF$_2$)+], 285 [(C$_3$F$_7$OCFCF$_3$)+], 217 [(CF$_2$OCFClCF$_2$Cl)+], 151 [(CFClCF$_2$Cl)+]. Anal. Calcd. for C$_{11}$F$_{22}$Cl$_2$O$_3$: C: 19.75, F: 62.48, Cl: 10.60; Found: C: 19.54, F: 61.62, Cl: 10.34. The minor product obtained in 15% yield could not be purified and is believed to be compound A based on its MS which shows peaks at m/e 85 [(CF$_2$CF$_2$Cl)+], 135 [(CF$_2$CF$_2$Cl)+], 201 [(CF$_2$OCF$_2$CF$_2$Cl)+], 379 [((ClCF$_2$CF$_2$OCF$_2$CF(CF$_3$)OCF$_2$CF)—F)+].

EXAMPLE 9

Preparation of Perfluoro(propyl vinyl) Ether
CF$_3$CF$_2$CF$_2$—O—CFCl—CF$_2$Cl→CF$_3$CF$_2$CF$_2$—O—CF=CF$_2$ Zinc dust (3.27 g, 0.05 mol) was suspended in N,N-dimethylformamide (DMF) (20 mL), activated with bromine (0.1 mL) and heated at 50° C. The dichloro ether starting material from Example 6 (8.43 g, 0.025 mol) was added slowly. After stirring 6 hr at 50° C., the volatile product from the reaction mixture was distilled and collected. A clear, colorless liquid was obtained, bp. 33° C., yield 3.6 g (54%). This highly pure product was proved to be the desired perfluoro(propyl vinyl) ether product by its $^{19}$F NMR spectrum and compared to the authentic sample.

EXAMPLE 10

Preparation of Perfluoro(pentyl vinyl) Ether

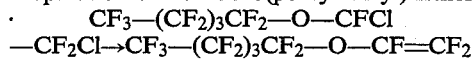

Zinc dust (1.31 g, 0.02 mol) was suspended in N,N-dimethylformamide (DMF) (10 mL), activated with bromine (0.1 mL) and heated at 50° C. The dichloro ether starting material from Example 7 (4.37 g, 0.01 mol) was added slowly. After addition, the pot temperature was raised to 80°–85° C. The reaction was allowed to proceed for 3 hr and the volatile product was distilled and collected, the pure title product was obtained as a clear, colorless liquid, bp. 36° C./24 kPa, yield 2.5 g (68.3%). The structure of the product was proved by its $^{19}$F NMR spectrum (188.24 MHz, CFCl$_3$): −81.4 (t, J=9.8 Hz, 3 F), −85.3 (s, br, 2 F), −113.3, −113.5, −113.6, −113.9 (4 s, 1 F), −121.5, −121.6, −121.8, −121.9 (4 s, 1 F), −123.6 (m, 2 F), −125.9 (d, J=9.8 Hz, 2 F), −126.8 (m, 2 F), −135.3, −135.5, −135.7, −135.9 (4 t, J= 8.8 Hz, 1 F). Mass for [M-CF=CF$_2$]: Calc.: 284.9774; Found: 284. 9825.

EXAMPLE 11

Preparation of Perfluoro[2,5-Bis (trifluoromethyl)-3,6-Dioxadecyl vinyl] Ether

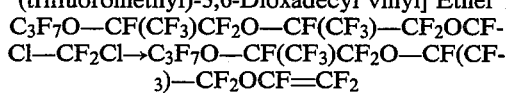

Zinc dust (0.72 g, 0.011 mol) was suspended in a mixed solvent of N,N-dimethylformamide (DMF) (5 mL) and anhydrous 1,4-dioxane (2.5 mL), activated with bromine (0.1 mL) and heated at 50° C. The dichloro ether starting material from Example 8 (2.5 g, 3.74 mmol) was added slowly. After addition, the reaction mixture was heated at 120°–130° C. for 8 hr. After cooling, the bottom product layer was separated and distilled to afford the pure title product as a clear, colorless liquid, bp. 85° C./11 kPa, yield 1.1 g. The structure of the product was proved by its $^{19}$F NMR spectrum (188.24 MHz, CFCl$_3$): −80.6 (m, 6 F), −82.1 (m, 3 F), −79.8 to −86.1 (m, 6 F), −113.6, −113.8, −113.9, −114.1 (4 m, 1 F), −121.9, −122.3, −122.4, −122.7 (4 s, br, 1 F), −130.3 (s, 2 F), −135.8, −136.1, −136.2, −136.5 (4 m, 1 F) −145.6 (m, 2 F); Anal. Calcd. for C$_{11}$F$_{22}$O$_3$: C: 22.08, F: 69.90; Found: C: 21.79, F: 69.90. Mass for [M]: Calc.: 597.9496; Found: 597.9499.

EXAMPLE 12

Preparation of 1,1-Dihydropentafluoropropyl 2-Iodo-1-Chlorotrifluoroethyl Ether

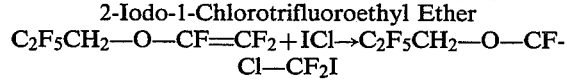

The neat vinyl ether (30.5 g, 0.133 mol) from Experiment 1 was placed in a flask cooled at 0°–5° C. in an ice bath. Iodine monochloride was added and the mixture was stirred at 0°–5° C., the dark brown color of the solution was gradually disappeared. More iodine monochloride (totally, 21 g, 0.129 mol) was added until the brown color was retained. The mixture was stirred overnight and distilled in the presence of small amounts of copper powder. The title compound was obtained as a pale pink liquid, bp. 90° C. at 23 kPa, yield 37 g (72.3%). $^1$H NMR (300 MHz, CDCl$_3$): δ4.24 (m); $^{19}$F NMR (188.24 MHz, CFCl$_3$): −58.3 (m, 2 F), −71.3 (s, 1 F), −83.9 (s, 3 F), −123.7 (t, J=10.6 Hz, 2 F). Anal. Calcd. for C$_5$H$_2$ClF$_8$IO: C: 15.30, H: 0.51, Cl: 9.03, F: 38.73; Found: C: 15.24, H: <0.5, Cl: 8.66, F: 38.15. Mass m/e: [M]: 392.

What is claimed is:

1. A process for the production of perfluoro(alkyl vinyl ethers), comprising, fluorinating with elemental fluorine a first compound of the formula R$^1$CHX$^3$OCX$^1$X$^2$CX$^1_2$X$^2$, to form a second compound of the formula R$^2$CF$_2$OCFX$^2$CF$_2$X$^2$, and dehalogenating said second compound to form a perfluoro(alkyl vinyl ether) of the formula R$^2$CF$_2$OCF=CF$_2$, wherein:

R$^1$ is hydrogen, a fluorinated alkyl group, or a fluorinated alkyl group containing one or more ether oxygen atoms between alkylene segments;

each X$^1$ and X$^3$ is independently hydrogen or fluorine;

in said first compound each X$^2$ is independently chlorine, bromine, iodine, or fluorine, provided that at least one of X$^2$ is chlorine;

in said second compound each X$^2$ is independently chlorine or fluorine, provided that at least one of X$^2$ is chlorine; and R$^2$ is fluorine, perfluoroalkyl, or perfluoroalkyl containing one or more ether oxygen atoms between alkylene segments.

2. The process as recited in claim 1 wherein R$^1$ is perfluoroalkyl, H(CF$_2$)$_n$— where n is 1 to 20, hydrogen, or perfluoroalkyl containing one or more ether oxygen atoms between alkylene segments.

3. The process as recited in claim 2 wherein R$^1$ is F(CF$_2$)$_n$— where n is 1 to 20, hydrogen, or C$_3$F$_7$O[CF(CF$_3$)CF$_2$O]$_y$CF(CF$_3$)—, wherein y is 0 or an integer of 1 to 8.

4. The process as recited in claim 2 wherein each X$^1$ is fluorine, each X$^2$ is chlorine, and X$^3$ is hydrogen.

5. The process as recited in claim 4 wherein said fluorinating is carried out at about −30° C. to about +50° C., using a solvent, a mixture of said elemental fluorine and an inert gas, and agitation.

6. The process as recited in claim 4 wherein said fluorination is carried out while being exposed to ultraviolet radiation.

7. The process as recited in claim 1 wherein each X$^1$ is fluorine, each X$^2$ is chlorine, and X$^3$ is hydrogen.

8. The process as recited in claim 1 wherein each X$^2$ is chlorine.

9. The process as recited in claim 8 wherein said first compound is prepared by chlorination of R$^1$CH$_2$OCF=CF$_2$ with Cl$_2$.

10. The process as recited in claim 1 wherein said fluorinating is carried out at about −30° C. to about +50° C.

11. The process as recited in claim 1 wherein said fluorinating is carried out using a solvent.

12. The process as recited in claim 1 wherein a mixture of said elemental fluorine and an inert gas is used.

13. The process as recited in claim 1 wherein agitation is used.

14. The process as recited in claim 1 wherein said fluorinating is carried out at about −30° C. to about +50° C., using a solvent, a mixture of said elemental fluorine and an inert gas, and agitation.

15. The process as recited in claim 1 wherein said dehalogenating is carried out with a metal or a metal reducing agent.

16. The process as recited in claim 1 wherein said dehalogenating is carried out with zinc, $TiCl_4/LiAlH_4$, magnesium or copper.

* * * * *